United States Patent [19]

Forwald et al.

[11] Patent Number: 5,128,116
[45] Date of Patent: Jul. 7, 1992

[54] SILICON POWDER AND METHOD FOR PRODUCTION OF SILICON POWDER

[75] Inventors: Karl Forwald, Kristiansand; Gunnar Schüssler, Drammen; Øyvind Sørli, Sewickley, all of Norway

[73] Assignee: Elkem a/s, Norway

[21] Appl. No.: 450,674

[22] Filed: Jan. 11, 1990

Related U.S. Application Data

[62] Division of Ser. No. 434,086, Nov. 9, 1989, abandoned.

[30] Foreign Application Priority Data

Dec. 8, 1988 [NO] Norway .................................. 885453

[51] Int. Cl.$^5$ ............................................. C01B 33/02
[52] U.S. Cl. .................................................. 423/348
[58] Field of Search ......................... 423/348, 349, 350

[56] References Cited

U.S. PATENT DOCUMENTS

| | | | |
|---|---|---|---|
| 3,592,391 | 7/1971 | Bender et al. | 75/0.5 R |
| 4,298,423 | 11/1981 | Lindmayer | 423/348 |
| 4,347,199 | 8/1982 | Spier et al. | 264/8 |
| 4,419,060 | 12/1983 | Spier et al. | 425/8 |
| 4,828,814 | 5/1989 | Sanjurjo et al. | 423/348 |

FOREIGN PATENT DOCUMENTS

47-18406 5/1972 Japan .

OTHER PUBLICATIONS

Himmelblau, "Basic Principles & Calc. in Che. Eng." 4th Ed., Prentice-Hall, Inc. New Jersey, p. 154.
Peters et al., "Plant Design & Economics for Che. Eng." 3rd Ed., McGraw-Hill Book Co., N.Y., pp. 33–34, 67.
Perry et al., "Perry's Chem. Eng. Handbook", 6th Ed. McGraw-Hill Book Co., N.Y., pp. 6-109, 20-77.

Primary Examiner—Olik Chaudhuri
Assistant Examiner—Kenneth E. Horton
Attorney, Agent, or Firm—Lucas & Just

[57] ABSTRACT

The invention relates to a method for continuous production of silicon powder comprising the combination of the following steps:
  a) continuous production of silicon in an electric smelting furnace,
  b) refining and alloying of the molten silicon in a metal treatment vessel,
  c) continuous supply of modern silicon from the metal treatment vessel to a holding furnace,
  d) continuous supply of molten silicon to a closed atomizing apparatus wherein the molten silicon is atomized by means of an inert gas supplied from a pressure vessel or a compressor unit,
  e) continuous removal of atomized silicon powder from the atomizing apparatus,
  f) separation of atomized silicon powder and inert gas in a solid/gas separator,
  g) screening of the silicon powder into preset particle size fractions,
  h) supply of the different particle size fractions of silicon powder to closed product silos,
  i) filtration of the inert gas from step f) for removing any remaining solid particles from the inert gas,
  cooling and compressing the inert gas from step i) and recycling of the compressed inert gas to the pressure vessel or directly to the atomizing apparatus.

17 Claims, 1 Drawing Sheet

SILICON POWDER AND METHOD FOR PRODUCTION OF SILICON POWDER

This is a division of application Ser. No. 434,086, filed Nov. 9, 1989, now abandoned.

The present invention relates to a new silicon powder product and to a continuous method for production of silicon powder.

Silicon is mainly produced by carbothermal reduction in electric furnaces. Molten silicon tapped from the furnaces is usually cast in the form of rather large blocks, for example by casting in cast iron moulds. For a number of different applications silicon is used in powder form and for these applications the blocks or pieces of silicon has to be mechanically crushed and thereafter grinded to a preset particle size having the desired chemical analysis. This method has, however, a number of disadvantages and drawbacks. Thus alloying elements which are added to the molten silicon and impurities contained in the molten silicon, show a strong tendency of segregation during block casting and the grain size in the solid silicon will be large due to the slow cooling rate which unavoidably will be obtained by block casting of silicon. During mechanical crushing and grinding of block cast silicon a nonhomogeneous powder product will thus be obtained due to segregation and large primary grain size, which for a number of applications is of disadvantage.

By block casting of silicon it will further be formed oxides, carbides, nitrides and carbonitrides. These compounds are, even in minor amounts unwanted.

The crushing and grinding processes also contaminate the silicon with iron due to wear of the crushing and grinding equipment.

During crushing and grinding of blocks of silicon the fracture surfaces of the silicon particles will oxidize and the produced powder will thus have an unwanted oxide layer on the surface of each individual particle.

Finally, the crushing and grinding processes constitute an environmental problem in the form of noise, dust and heat stress.

It has therefore been a need to provide a method for continuous production of silicon powder directly from molten silicon which is tapped from electrical smelting furnaces.

A large number of methods are known for production of metal powders in general, such as for example atomizing by means of an inert gas, atomizing by means of a liquid, atomizing on a rapidly rotating disk, etc. These known methods for production of metal powders are, however, batch processes where a certain amount of metal is melted and atomized, and is for this reason not economical viable, as it by use of these methods is not possible to continuously produce silicon powder directly from molten metal tapped from a smelting furnace, without going through the route of a normal casting process and remelting. As far as the inventors are aware a method for gas atomizing of silicon is not known.

The object of the present invention is to provide a silicon powder which does not show the above mentioned drawbacks of silicon powder made from block cast silicon and to provide a continuous method for production of silicon powder.

According to a first aspect, the present invention relates to a silicon powder which is characterized in that the silicon powder is produced by gas atomizing of molten silicon, which silicon powder has a particle size between 0.1 and 1000 μm, a specific surface area between 0.001 and 1 m$^2$/g and the following chemical composition in percent by weight:

0.1–1% iron
0.01–1% aluminium
0–8% copper
0–1% calcium
0–1% zinc
0–1% tin
0–0.5% boron
0–0.5% phosphorus
0–0.5% sodium
0–0.5% lithium
0–0.5% potassium
0–0.5% magnesium
0–0.5% strontium
0–0.5% barium
0–0.5% beryllium the rest being silicon and less than 0.3% impurities such as Ti, V, Cr, Mo, W and Zr.

According to a preferred embodiment the silicon powder has the following composition in percent by weight: 0.25–0.55% iron, 0.05–0.45% aluminium, 0.005–0.20% calcium, the rest being silicon except for normal impurities as described herein.

According to another preferred embodiment the silicon powder has the following composition in percent by weight: 0.25–0.55% iron, 0.05–0.45% aluminum, 0.005–0.20% calcium, 1–6% copper, the rest being silicon except for normal impurities as described herein.

The silicon powder according to the present invention is especially suited for use in the production of organosilanes where silicon powder is reacted with an alkyl- or aryl chloride, and for the production of chlorosilanes.

For production of organosilanes silicon powder is reacted with an alkyl- or arylchloride in the presence of a copper catalyst and promoters such as zinc and tin. It has been found that by using silicon powder according to the present invention a strongly increased production rate is obtained during the silane production. A particular advantage by use of the silicon powder according to the present invention in production of organosilanes is that copper catalyst and promoters such as zinc and tin can be present in the silicon powder itself.

The silicon powder according to the present invention is further advantageously used in ceramic and refractory materials and for alloying aluminium by injection of silicon powder into aluminium melts.

According to another aspect, the present invention relates to a method for continuously production of silicon powder, the method being characterized by the combination of the following steps:

a) continuous production of silicon in an electric smelting furnace, b) refining and alloying of the molten silicon in a metal treatment vessel, c) continuous supply of molten silicon from the metal treatment vessel to a holding furnace.

d) continuous supply of molten silicon from the holding furnace to a closed atomizing apparatus, wherein the molten silicon is atomized by means of an inert gas supplied from a pressure vessel or from a compressor unit, e) continuous removal of atomized silicon powder and inert gas from the atomizing apparatus, f) separation of atomized silicon powder and inert gas in a solid/gas separator,
g) screening of the silicon powder to preset particle size fractions,
h) supply of the different particle size fractions of silicon powder to closed production silos,
i) filtration of the inert gas from step f) for removing any remaining solid particles from the inert gas,
j) cooling and compressing the inert gas from the step i) and recycling of the compressed inert gas to the pressure vessel or directly to the atomizing apparatus.

According to a preferred embodiment of the method chemical compounds for modifying the surface of the atomized silicon particles are injected at the outlet end of the atomizing apparatus, between the atomizing apparatus and the solid/gas separator or inside the solid/gas separator.

By the method according to the present invention silicon is treated in a closed system and in an inert atmosphere, from when molten silicon is supplied to the atomizing unit in step d) until the screened silicon powder has been supplied to the product silos. The possibility of supplying impurities to the silicon powder has thus been eliminated.

BRIEF DESCRIPTION OF THE FIGURE

The method according to the present invention will now be further described in connection with the accompanying drawing where.

DETAILED DESCRIPTION OF THE INVENTION

Figure 1:
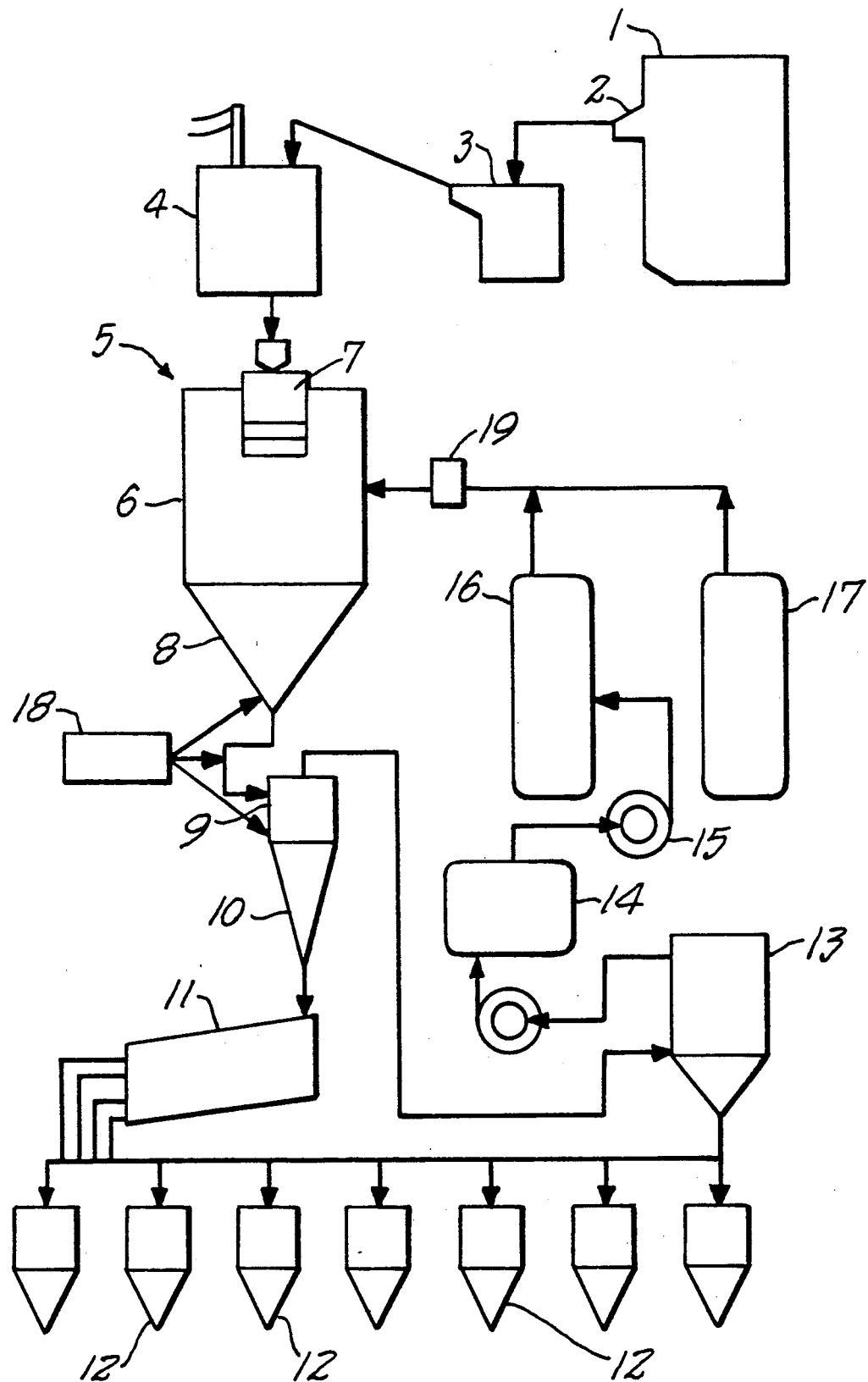
FIG. 1 shows a schematic view of the method according to the present invention.

In FIG. 1 there is shown an electric smelting furnace 1 for carbothermal production of silicon from a silicon dioxide source and carbonaceous reduction material. Molten silicon is continuously tapped from the smelting furnace 1 at 2 and is transferred to a treatment vessel 3 wherein the silicon is refined and alloyed in conventional manner. Thereafter the treated molten silicon is transferred to a holding furnace 4. From the holding furnace 4 a continuous and constant or substantially constant amount of silicon is supplied to an atomizing apparatus 5.

The atomizing apparatus 5 comprises a closed tank 6 in the upper part of which there is arranged an atomizing unit 7 having a plurality of nozzles for supply of inert gas which breaks up the continuous flow of silicon into small molten droplets which solidifies during free fall down through the tank 6.

In the atomizing apparatus 5 the silicon solidifies in the course of a few seconds. This gives very homogeneous silicon particles without segregation and, due to the inert atmosphere, oxides, carbides, nitrides or carbonitrides are not formed in the particles. A clean and homogeneous powder is thereby obtained.

The silicon powder is collected in the bottom 8 of the tank 6. From the bottom 8 of the tank 6 the silicon powder and inert gas are supplied to an apparatus 9 for separation of powder and inert gas. The apparatus 9 is preferably a cyclone. From the bottom 10 of the apparatus 9 for separation of powder and inert gas, silicon powder is coninuously supplied to a closed screening unit 11 for screening the powder into different size fractions. The different size fractions of silicon powder are thereafter transported in a closed system to product silos 12 for silicon powder.

As will be evident from the above, the silicon powder is transported in a closed system having an inert atmosphere from when the powder is formed in the atomizing apparatus 5 until the powder is supplied to the product silos 12. Surface oxidation of the individual particles will therefore not take place.

From the apparatus 9 for separating silicon powder and inert gas, the inert gas is forwarded to a filter 13, preferably a bag filter wherein any remaining silicon particles are removed and transported to one of the product silos 12. The cleaned inert gas is forwarded to a cooler 14 for cooling the gas before the gas is compressed in a compressor 15 and supplied to a pressure tank 16 for inert-gas. From the pressure tank 16 the inert gas is recirculated to the nozzles in the atomizing unit 7.

Before start-up of the atomizing process it is necessary to remove all oxygen-containing gas from the closed system. For this purpose a second pressure tank 17 for inert gas is provided. Further, after the filter 13 there is arranged a bleeding valve for bleeding out the gas used to remove oxygen-containing gases before start-up. The pressure tank 17 is further used to supply additional amount of inert gas to compensate for the amount of inert gas which during the atomizing process is lost to the screening unit and to the product silos. This loss is, however, very low and normally less than 1% of the gas which is supplied to the atomizing unit 7.

Between the bottom 8 of the atomizing tank 6 and the apparatus 9 for separating silicon powder and inert gas, it is preferably arranged means 18 for addition of compounds for modifying the surface of the silicon powder particles.

In order to regulate the amount of inert gas to the atomizing nozzles in relation to the amount of molten silicon supplied to the atomizing apparatus 5, there is arranged a control unit 19 for automatic regulation of the gas volume.

In the following examples the advantages obtained by using the silicon powder according to the present invention in production of organosilanes by reaction of silicon with methyl chloride is shown.

EXAMPLE 1

In a stirred bed reactor having a diameter of 30 mm and equipped with a spiral stirrer, the following tests were carried out.

In all tests the same amount of silicon or copper alloyed silicon was used. The particle size of the silicon was between 70 and 160 μm. Methyl chloride at a pressure of 2 bar was supplied to the bottom of the reactor. The amount of methyl chloride was kept constant and was in all tests about 1.5 liter/hour at 2 bar. After preheating and initiating of the reaction a stationary test-phase was established at 300° C. Under these conditions the produced amount of silanes per time unit was measured. The results given are mean values of four tests at constant conditions of 2 bar, 1.5 liter/hour methyl chloride and 300° C. The contact mass supplied to the reactor comprised 40 grams silicon, 3.2 grams copper catalyst and 0.05 g ZnO. The mass was homogenized before it was added to the reactor.

Tests A and B were run with silicon powder produced in a conventional way by crushing and grinding. Test C was run with silicon powder produced in accordance with the present invention.

The chemical composition of the silicon used in tests A, B and C were as follows:

|   | A<br>% by weight | B<br>% by weight | C<br>% by weight |
|---|---|---|---|
| Fe | 0.43 | 0.3 | 0.52 |
| Al | 0.32 | 0.19 | 0.38 |
| Ca | 0.07 | 0.10 | 0.08 |

The following production rates of silanes were obtained in the three tests:
Test A: 5.7 gram/hour
Test B: 5.2 gram/hour
Test C: 8.3 gram/hour The results show that by using the atomized silicon powder according to the present invention an increase in production rate of 45%, respectively 56% was achieved compared to conventional silicon powder.

EXAMPLE 2

To the same reactor as described in example 1 and under the same conditions (2 bar, 1.5 liter/hour methyl chloride and 300° C.) it was supplied atomized silicon powder according to the present invention having the following chemical composition in percent by weight:

Fe:0.34% Al:0.40% Cu:5.75% Zn:0.14% Ca:0.10% the rest being silicon except for impurities. The production rate of silanes in two test runs was measured to 8.13 gram/hour, respectively 9.9 grams/hour and shows a strong increase in the production rate compared to the use of conventional crushed and grinded silicon in tests A and B in example 1.

What is claimed:

1. A method for continuous production of silicon powder, characterized by the combination of the following steps:
   a) continuous production of silicon in an electric smelting furnace;
   b) refining and alloying of the molten silicon in a metal treatment vessel;
   c) continuous supply of molten silicon from the metal treatment vessel to a holding furnace;
   d) continuous supply of molten silicon to a closed atomizing apparatus wherein the molten silicon is atomized under inert conditions by means of an inert gas supplied from a pressure vessel or a compressor unit;
   e) continuous removal of atomized silicon powder from the atomizing apparatus;
   f) separation of atomized silicon powder and inert gas in a solid/gas separator;
   g) screening of the silicon powder into different particle size fractions, each fraction being of a different particle size;
   h) supply of the different particle size fractions of silicon powder to closed product silos;
   i) maintaining an inert atmosphere about said atomized silicon powder from the step wherein said molten silicon is atomized through the step of supplying said silicon powder to said closed product silo;
   j) filtration of the inert gas from step f) for removing any remaining solid particles from the inert gas; and
   k) cooling and compressing the insert gas from step j) and recycling of the compressed inert gas to the pressure vessel or directly to the atomizing apparatus.

2. Method according to claim 1, characterized in that chemical compounds for modifying the surface of the atomized silicon particles are injected at the outlet end of the atomizing apparatus, between the atomizing apparatus and the solid/gas separator or inside the solid/gas separator.

3. A method for the continuous production of silicon powder comprising the following steps:
   a) continuously producing molten silicon in a smelting furnace;
   b) refining and alloying said molten silicon;
   c) continuously supplying said molten silicon to a closed atomizing apparatus, said molten silicon being atomized in said atomizing apparatus under inert conditions by means of an inert gas to form atomized silicon powder;
   d) continuously removing said atomized silicon powder from said atomizing apparatus;
   e) separating in a separator said atomized silicon powder from said inert gas;
   f) screening in a screening apparatus said silicon powder according to size into silicon powder particle size fractions;
   g) supplying each said silicon powder particle size fraction to a closed product silo;
   h) filtering in a filtering apparatus said inert gas after separation from said silicon powder to remove any remaining silicon powder;
   i) supplying said remaining silicon powder from said filtering apparatus to said closed product silo;
   j) maintaining an inert atmosphere about said silicon powder and said remaining silicon powder from the step wherein said molten silicon is atomized through the step of supplying said silicon powder and remaining silicon powder to said closed product silo;
   k) cooling and compressing said filtered inert gas; and
   l) recycling said compressed inert gas to said atomizing apparatus.

4. The method of claim 3 wherein said molten silicon is held in a holding furnace before supply to said closed atomizing apparatus.

5. The method of claim 3 wherein said inert gas is supplied by a pressure vessel.

6. The method of claim 3 wherein said atomized silicon powder is separated from said inert gas in a cyclone.

7. The method of claim 4 wherein said compressed inert gas is recycled to said pressure vessel before supply to said atomizing apparatus.

8. The method of claim 3 wherein chemical compounds for modifying the surface of said atomized silicon powder particles are applied to said particles.

9. The method of claim 8 wherein said chemical compounds are applied to said silicon powder particles at a location selected from the group consisting of the outlet end of said atomizing apparatus; between said atomizing apparatus and said separator; and inside said separator.

10. The method of claim 3 wherein oxygen-containing gas is removed from said closed atomizing apparatus, said separator, said screening apparatus, and said filtering apparatus before molten silicon is supplied to said closed atomizing apparatus.

11. The method of claim 3 further comprising a control unit for controlling the amount of said inert gas supplied to said atomizing apparatus depending upon the amount of said molten silicon to be atomized.

12. A method for production of substantially pure silicon powder directly from molten silicon taken from an electric smelting furnace comprising the steps of:
  a) tapping a smelting furnace which contains molten silicon to obtain molten silicon;
  b) atomizing in a closed atomizing apparatus under inert conditions using an inert gas said molten silicon which had been tapped from said smelting furnace such that said molten silicon has not solidified after being tapped from said smelting furnace to produce a substantially pure silicon powder; and
  c) recovering under inert conditions said substantially pure silicon powder.

13. The method of claim 12 wherein after step (a) and prior to step (b) said molten silicon is subjected to a step of refining and re-alloying said molten silicon.

14. The method of claim 12 wherein step (c) comprises:
  $c_1$) continuously removing said substantially pure silicon powder and said inert gas from said atomizing apparatus;
  $c_2$) separating in a separating apparatus said substantially pure silicon powder from said inert gas;
  $c_3$) screening in a screening apparatus said silicon powder according to size into silicon powder particle size fractions;
  $c_4$) filtering in a filtering apparatus said inert gas separated from said substantially pure silicon powder in step ($c_2$) to remove any remaining silicon powder;
  $c_5$) supplying to closed silos said silicon powder particle size fractions from step ($c_3$) and said remaining silicon powder from step ($c_4$); and
  $c_6$) maintaining an inert atmosphere about said silicon powder and remaining silicon powder from atomization through said closed silo.

15. The method of claim 12 further comprising the step of recovering said inert gas used in step (b) and recycling the recovered inert gas for use in said atomizing apparatus.

16. The method of claim 14 further comprising the step of recycling said inert gas from step ($c_4$) for re-use in said atomizing apparatus.

17. The method of claim 16 wherein said recycling comprises the steps of cooling said inert gas from step ($c_4$); compressing the cooled inert gas; and supplying the cooled and compressed inert gas to said atomizing apparatus.

* * * * *

UNITED STATES PATENT AND TRADEMARK OFFICE
CERTIFICATE OF CORRECTION

PATENT NO. : 5,128,116

DATED : July 7, 1992

INVENTOR(S) : Karl Forwald et al.

It is certified that error appears in the above-identified patent and that said Letters Patent are hereby corrected as shown below:

On the title page: change [75] Inventors: to read:
--Karl Forwald, Kristiansand, Gunnar Schüssler, Drammen; all of Norway, Øyvind Sørli, Sewickley, Pennsylvania--

Abstract, line 1, after "The" insert --present--; line 8, change "modern" to --molten--; line 24, before "cooling" insert --j)--.

Column 1, line 16, change "has" to --have--; line 32, after "amounts" insert --,--; line 43, change "It" to --There--; line 53, change "is" to --are--.

Column 2, line 53, change "continuously" to --continuous--; line 61, change "." to --,--.

Column 3, line 64, change "coninuously" to --continuously--.

Column 4, line 22, after "supply" insert --an--; line 31, change "it" to --there--; line 42, change "is" to --are--, line 67, change "composition" to --compositions--.

UNITED STATES PATENT AND TRADEMARK OFFICE
CERTIFICATE OF CORRECTION

PATENT NO. : 5,128,116
DATED : July 7, 1992
INVENTOR(S) : Karl Forwald et al.

It is certified that error appears in the above-identified patent and that said Letters Patent are hereby corrected as shown below:

Column 5, line 22, delete "it was supplied"; line 24, after "weight" insert --was supplied--.

Claim 5, clause k), line 1, change "insert" to --inert--.

Signed and Sealed this

Twenty-fourth Day of August, 1993

Attest:

Attesting Officer

BRUCE LEHMAN

Commissioner of Patents and Trademarks